(12) United States Patent
Hung et al.

(10) Patent No.: US 9,637,430 B2
(45) Date of Patent: May 2, 2017

(54) STAGED SYNTHESIS OF DIIODOPERFLUORO-$C_3$ TO $C_7$-ALKANES

(71) Applicant: THE CHEMOURS COMPANY FC, LLC, Wilmington, DE (US)

(72) Inventors: Ming Hong Hung, Wilmington, DE (US); Alexander Anthony Marchione, Haddon Heights, NJ (US); Peter A. Morken, Wilmington, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 15/053,699

(22) Filed: Feb. 25, 2016

(65) Prior Publication Data

US 2016/0251284 A1    Sep. 1, 2016

Related U.S. Application Data

(60) Provisional application No. 62/126,320, filed on Feb. 27, 2015.

(51) Int. Cl.
*C07C 17/26* (2006.01)
*C07C 17/272* (2006.01)
*C07C 17/20* (2006.01)
*C07C 17/093* (2006.01)

(52) U.S. Cl.
CPC .......... *C07C 17/272* (2013.01); *C07C 17/093* (2013.01); *C07C 17/204* (2013.01); *C07C 17/26* (2013.01)

(58) Field of Classification Search
None
See application file for complete search history.

(56) References Cited

U.S. PATENT DOCUMENTS

| 4,948,852 A | 8/1990 | Moore |
| 5,231,154 A | 7/1993 | Hung |
| 6,002,055 A | 12/1999 | Yang |
| 6,277,937 B1 | 8/2001 | Duvalsaint et al. |
| 6,825,389 B2 | 11/2004 | Dindi et al. |

FOREIGN PATENT DOCUMENTS

| WO | 2014/062450 A2 | 4/2014 |
| WO | 2014/062469 A1 | 4/2014 |

OTHER PUBLICATIONS

Yang, Zhen-Yu, Nickel-Catalyzed Reaction of Highly Fluorinated Epoxides with Halogens, Journal of American Chemical Society, 1996, pp. 8140-8141, vol. 118.
Yang, Zhen-Yu, Preparation of Highly Fluorinated Cyclopropanes and Ring-Opening Reactions with Halogens, Journal of Organic Chemistry, 2003, pp. 4410-4416, vol. 68.

*Primary Examiner* — Jafar Parsa
*Assistant Examiner* — Medhanit Bahta

(57) ABSTRACT

The process is provided for forming the reaction product comprising the homologue mixture of $I(CF_2)_nI$, wherein n is 3 to 7, which may contain at least one of the contaminants $ICF_2I$ and $I(CF_2)_2I$, by the steps comprising (a) reacting iodine with hexafluoropropylene oxide at a temperature of 150° C. to 210° C. in a reactor, the amount of said hexafluoro-propylene oxide being a portion of the total amount of hexafluoropropylene oxide to be reacted with said iodine, thereby forming a reaction product containing gaseous perfluoroacetyl fluoride as a reaction by-product, (b) cooling said reaction product to become liquid except for said gaseous perfluoroacetyl fluoride, (c) venting said perfluoroacetyl fluoride from said reactor, and (d) repeating said steps (a), (b), and (c) until said total amount of said HFPO is reacted with said iodine.

9 Claims, No Drawings

STAGED SYNTHESIS OF DIIODOPERFLUORO-$C_3$ TO $C_7$-ALKANES

BACKGROUND INFORMATION

Field of the Disclosure

This invention relates to the synthesis of diiodoperfluoro-$C_3$ to $C_7$-alkanes ($I(CF_2)_nI$, wherein n is 3 to 7, under moderate pressure conditions.

Description of the Related Art

Examples 1 through 11 of U.S. Pat. No. 6,002,055 disclose the reaction of hexafluoropropylene oxide (HFPO) with iodine under autogenous pressure in a reactor at 185° C., with and without the presence of a catalyst, to obtain diiodomethanes and their homologues. The HFPO/iodine reaction is disclosed in the reaction equation (II) (col. 3, I. 25) to form one mol of $CF_3COF$ (perfluoroacetyl fluoride) (PAF) by-product for each mol of HFPO consumed in the reaction. Example 1 discloses the formation of 184 g of PAF from 266 g of HFPO reactant. The problem presented by the formation of the PAF in the reactor as a result of the HFPO/iodine reaction is that the PAF, especially towards the end of the reaction when the PAF formation is approaching its peak, causes the autogenous pressure within the reactor to become very high, requiring the use and expense of a high pressure resistant reactor and auxiliary equipment including seals.

WO 2014/062450 discloses the HFPO/iodine reaction being carried out in the presence of certain combinations of Ni and Mo as a catalyst that minimize the production of $I(CF_2)_nI$, wherein n is 1 or 2 during the synthesis of $I(CF_2)_nI$, wherein n is 3 to 11. In the Examples of the invention, the reaction is carried out at temperatures of 170° C. to 185° C. (Examples 1-3 and the batch temperatures in Table 4). No mention is made of the formation of PAF in the reaction even though its formation is inevitable. COMPARATIVE EXAMPLE A, however, discloses the cooling of the reaction autoclave to room temperature, followed by the venting of gases. This venting would include the total amount of PAF formed in the reaction.

SUMMARY

The present invention enables the HFPO/iodine reaction to be conducted at moderate pressures, substantially less than heretofore. This enables the reaction to be carried out in a lower pressure-operated reactor, including associated equipment, thereby providing a savings in manufacturing setup.

The process of the present invention forms the reaction product comprising the homologue mixture of $I(CF_2)_nI$, wherein n is 3 to 7, which contains at least one of the contaminants $ICF_2I$ and $I(CF_2)_2I$, by the steps comprising
(a) reacting iodine with hexafluoropropylene oxide (HFPO) at a temperature of 150° C. to 210° C. in a reactor, the amount of said HFPO being a portion of the total amount of HFPO to be reacted with said iodine, thereby forming a reaction product containing gaseous perfluoroacetyl fluoride (PAF) as a reaction by-product,
(b) cooling said reaction product to become liquid except for said gaseous perfluoroacetyl fluoride,
(c) venting said perfluoroacetyl fluoride from said reactor,
(d) repeating said steps (a), (b), and (c) until said total amount of said HFPO is reacted with said iodine,
and obtaining as a result thereof said reaction product comprising said homologue mixture.

Instead of postponing the venting (removal) of the PAF until completion of the reaction, the process of the present invention vents the PAF at intervals in the carrying out of the HFPO/iodine reaction. If the sequence of steps (a) through (c) is carried out three times, with the portion of HFPO being present at the start of each step (a) being ⅓ the total amount of HFPO used, the increase in autogenous pressure within the reactor attributed to the formation of PAF will be moderated to be only ⅓ the pressure increase when PAF venting is postponed until completion of the reaction carried out in a single stage as exemplified in U.S. Pat. No. 6,002,055 and WO 2014/062450. The repetition of steps (a) in accordance with the present invention means that the synthesis of the reaction product described above is in stages. The process of the present invention, taking all of the steps (a) through (d) into account, can also be referred to as a vent-charge process, i.e. venting PAF and charging additional HFPO to the reactor.

Preferably, the portion of the HFPO reacted in each of said step (a) is from 10 to 50% of said total amount of the HFPO reacted with the iodine.

Preferably, the molar proportion of the total amount of the HFPO reacted with the iodine is at least 3.0.

Preferably, the yield of the reaction product is at least 70%.

Preferably, the homologue mixture of $I(CF_2)_nI$, wherein n is either 1 to 7 or 3 to 7 in the reaction product resulting from the carrying out of the process of the present invention comprises at least 90% (GC area) of the reaction product.

Preferably, the contaminants $ICF_2I$ and $I(CF_2)_2I$ are present in the reaction product in amounts of no greater than 1% (GC area) and no greater than 0.1%, respectively.

The process of the present invention is preferably carried out under conditions effective to obtain these results, individually and collectively. A preferred condition is to carry out each step (a) in the presence of a catalyst that is effective to obtain these results. Alternatively or in combination with a catalyst being present in the reaction in each step (a), the reaction product is heated to at least 220° C. at least after the last step (a) of said repeating said steps (a), (b) and (c).

These preferences can be practiced individually or in any combination in the process of the present invention.

DETAILED DESCRIPTION

The yield % amounts disclosed herein are a comparison of weights as described in the Examples.

The % amounts of $I(CF_2)_nI$, compounds disclosed herein, whether referring to n being 1 or 2 or being any member of the homologous mixture n=3 to 7 or n=3 to 7 collectively, or the like refers to the peak area corresponding to the particular compound compared to all other peak areas under the curve obtained by gas chromatograph analysis (GC) of the reaction product being analyzed. Thus, this % amount may also be referred to as the GC area % or simply area %. The GC area % is an approximation of mol %.

The process of the present invention is preferably carried out in a reactor under the autogenous pressure of the chemical reaction occurring in step (a). In the chemical reaction between iodine and HFPO, both gaseous at the temperature of the chemical reaction, the PAF gaseous by-product is a substantial contributor to the autogenous pressure developing within the reactor. This contribution is reported in Table 1 below and amounts to a 100% increase in pressure when the HFPO/iodine reaction is carried out in a single stage, followed by a single venting of the PAF from the reactor.

The temperature to which the reactor is heated in step (a) is preferably from 170° C. to 200° C., this lower temperature minimizing unwanted side reactions.

The molar ratio of HFPO to iodine in the chemical reaction is preferably at least 3.0, more preferably at least 3.3, still more preferably at least 3.4, and even more preferably, at least 3.5. Preferably, the molar ratio of HFPO to iodine is no greater than 3.8. These molar ratios apply to the total amount of HFPO charged into the reactor for all of the steps (a) of the process.

Only a portion of the total amount of HFPO to be reacted is present in the practice of the first step (a), and additional portions of the HFPO are added in each repetition of step (a) to reach the remainder of the total amount of HFPO to be reacted. Thus, the subsequent reacting steps (a) include the addition (charging) of additional portions of HFPO to be consumed in the reaction with iodine. The reaction in each step (a) is preferably carried out to 100% conversion of the HFPO reactant, whereby there is no need to recover unreacted HFPO that would otherwise vent along with the PAF in step (c).

More preferably, the portion of HFPO added to and present in the reactor for reaction with the iodine in each step (a) of the process of the present invention is 20 to 50% of the total amount of HFPO reacted with the iodine, even more preferably 33 to 50%. Preferably the portion of HFPO reacted in each step (a) is in the same amount.

Preferably, the total amount of iodine to be reacted is added to the reactor so as to be present in the first step (a).

Each cooling step (b) is conveniently carried out by cooling of the reactor contents to 0° C. At this temperature, the PAF in the reaction product remains gaseous, while the $I(CF_2)_nI$ homologue mixture, wherein n is 1 to 7, is in the liquid state, enabling the PAF to be separated from the liquid reaction product by venting from the reactor. No HFPO, boiling temperature −27.4° C., is vented with the PAF, because the HFPO has preferably been reacted with the iodine in the reactor.

Preferably, the yield of the reaction product is at least 75%, more preferably at least 80%, and even more preferably, at least 85%, and most preferably, at least 90%.

Preferably, the homologue mixture of $I(CF_2)_nI$, wherein n is either 1 to 7 or 3 to 7 in the reaction product resulting from the carrying out of the process of the present invention comprises at least 92% (GC area) of the reaction product on which GC analysis is done. Preferably the compound $I(CF_2)_3I$ comprises at least 70% (GC area) of this reaction product, more preferably at least 80%, and even more preferably at least 90% of both the reaction product and the above-mentioned homologue mixture of compounds.

Preferably, the contaminants $ICF_2I$ and $I(CF_2)_2I$ are present in amounts of no greater than 1% and no greater than 0.1%, respectively, in the reaction product. The wording "amounts of no greater than 1% and no greater than 0.1, respectively" is intended to include no measureable amounts of either or both contaminants in the reaction product.

The process of the present invention is carried out to obtain the foregoing mentioned results, individually and collectively.

In one (first) embodiment aimed at obtaining these results, each step (a) is carried out in the presence of a catalyst such as disclosed in U.S. Pat. No. 6,002,055 and WO 2014/062450, the disclosures of which are incorporated herein by reference. The catalyst is selected along with the other reaction conditions to be effective to provide these results. '450 discloses the catalyst to be a combination of two metals, Ni and Mo or a Ni/Mo alloy of 50 to 70 wt % Ni and 20 to 40 wt % Mo based on the total weight of the alloy. Example 2 of '450 discloses the use of a Hastelloy B2 lined reactor, the Hastelloy containing 28 wt % Mo and 6.89 wt %, together and Nickel Catalyst 2, which is a Ni ribbon containing tiny holes, added into the reactor in which the HFPO/iodine reaction is carried out in a single stage to obtain the smallest amounts of $ICF_2I$ and $I(CF_2)_nI$. Such a catalyst and others that are effective to provide the high selectivity towards the formation of the homologous mixture of compounds $I(CF_2)_nI$, wherein n is 3 to 7, accompanied by little to no formation of $ICF_2I$ and $I(CF_2)_2I$ can be used in the staged synthesis process of the present invention. Periodic venting of the PAF by-product from this reaction enables the catalyzed HFPO/iodine reaction to be carried out at a lower autogenous pressure than if the reaction were conducted and completed in a single stage, wherein the maximum amount of PAF would be formed and present within the reactor.

According to one aspect of this first embodiment, the reaction in each step (a) is carried out in the absence of added catalyst. The absence of added catalyst means to the absence of catalyst added within or into the chemical reaction carried out in the reactor. The interior surface such as a lining of the reactor, if the interior surface were a catalyst, it is not an added catalyst, because the interior surface borders the chemical reaction and therefore is not within the chemical reaction. Another aspect of this first embodiment is that the reaction in each step (a) can be carried out in a reactor, the interior surface of which is a catalyst for the HFPO/iodine reaction. According to this aspect, the reaction in each step (a) is carried out in the presence of catalyst but in the absence of added catalyst.

In another (second) embodiment aimed at obtaining the above described results, the reaction product in step (a) is heated to at least 220° C. at least after the last step (a) of the repeating steps (a), (b) and (c).

This heating up from the temperature at which the HFPO/iodine reaction is carried out is preferably from 220° C. to 240° C., more preferably from 225° C. to 240° C. The effect of this heating up from the reaction temperature is to decompose the $ICF_2I$ and $I(CF_2)_2I$ formed in the step (a) reaction. This heating up is carried out for an effective amount of time to achieve the decomposition desired, without decomposing the desired homologous mixture of compounds $I(CF_2)_nI$, wherein is 3 to 7. Preferably this heating up reduces the amount of $ICF_2I$ and $I(CF_2)_2I$ by at least to ⅓, more preferably by at least to ⅕, and even more preferably by at least to 1/10 the amount present in the reaction product prior to the heating up.

Preferably, the heating up obtains the result of the contaminants $ICF_2I$ and $I(CF_2)_2I$, when one or both are present, being present in amounts of no greater than 1% (GC area) and no greater than 0.1%, respectively, in the reaction product.

In one aspect of this second embodiment, the heating up to a temperature of at least 220° C. can be carried out as part of each step (a), i.e. after the reaction is carried out at a temperature in the range of 150° C. to 210° C., preferably 170° C. to 200° C., and prior to step (b). Alternatively, the heating step can be carried out only one time as part of the last step (a) prior to the last step (b), i.e. on the reaction product after the reaction of all the steps (a) have been conducted in the repetitions of steps (a), (b), and (c).

The practice of the first and second embodiments can be combined. Preferably, in this combination of embodiments, the second embodiment is the aspect wherein the reaction in each step (a) is carried out in the absence of added catalyst.

Instead, the reaction in each step (a) is preferably carried out in the presence of catalyst that is not added catalyst, i.e. in the presence of catalyst that forms the interior surface of the reactor within which the step (a) reactions are carried out. This reaction is then carried out in the presence of catalyst and the absence of added catalyst.

EXAMPLES

In the Examples, the diiodoperfluoroallkanes may be referred to as the following:
PDA-1=$ICF_2I$
PDA-2=$I(CF_2)_2I$
PDA-3=$I(CF_2)_3I$
PDA-4=$I(CF_2)_4I$
PDA-5=$I(CF_2)_5I$
PDA-6=$I(CF_2)_6I$
PDA-7=$I(CF_2)_7I$ The gas chromatography GC analysis results whether disclosed as %, GC area %, or as area % with respect to one or more compounds ($I(CF_2)_nI$, wherein is 1 to 7, are obtained using an Agilent 7890 gas chromatography (GC) system (Santa Clara, Calif.), using a 20% OV-210 packed column (Supelco, Bellefonte, Pa.), with a straight isothermal 160° C. temperature condition, along with a thermal conductivity (TCD) detector. The GC area % of the homologue mixture of the above compounds is the selectivity of the formation of the compound(s) referred to, e.g. the mixture wherein n is 3 to 7 or n is 3 by itself. The reactor used in the Examples is made of Hastelloy® C, a metal alloy containing in wt % 56% Ni, 3.5% W, 6.2% Fe, 16.5% Cr, 17% Mo, and less than 1% amounts of C, V, Mn, Si, P, and S.

Yield % is the comparison of the actual weight of the reaction product with the theoretical weight of the reaction product.

Calculation: % yield=(actual weight÷theoretical weight)×100

The actual weight of the reaction product is the weight after venting of the PAF by-product of the product of the reaction, followed by washing of the remainder of this direct reaction product to obtain the purified reaction product. The theoretical weight of the reaction product is obtained from the following calculation: the weight of the iodine+the weight of the $CF_2$ (difluorocarbene) from the HFPO (=(50/166)×wt. of HFPO.

The GC analysis results are taken from CG analysis on the purified reaction product after (i) removal of perfluoroacetyl fluoride (PAF) by cooling the direct reaction product to 0° C. and (ii) venting the gas from the reactor and (iii) then washing of the remaining reaction product. PAF boils at −59° C.

The washing referred to herein is carried out using an aqueous solution that is iodine removing, whereby the washing of the remaining reaction product to remove the trace amounts of unreacted iodine and any water soluble materials. The aqueous solution can be for example, a saturated solution of sodium bisulfite. The washing is conveniently carried out at ambient temperature (15° C. to 25° C.).

At the completion of the HFPO/iodine reaction, after the final removal (venting) of PAF, it can be considered that there are two reaction products, as follows: (1) the reaction product obtained directly from the reaction, i.e. the direct reaction product, and (2) the reaction product resulting from washing of the direct reaction product such as with saturated aqueous solution of sodium bisulfite at ambient temperature (15° C. to 25° C.). The reaction product (2) is the purified reaction product mentioned above. The weight loss from this wash is very little as compared to the weight of the direct reaction product (1). In the % yield calculation, the actual weight of the reaction product is the weight of the purified reaction product.

The temperature at which the HFPO/iodine reaction is carried out, also referred to herein as the reaction temperature or the temperature to which the reactor content is heated, and the temperature of heating to at least 220° C. to decompose the compounds $ICF_2I$ and $I(CF_2)_2I$, as disclosed herein, all refer to the temperature of the content of the reactor, i.e. temperature of the interior of the reactor. In the small reactor (tube) used in the Examples, the temperature of the reactor and its content are the same, as determined by comparison of temperature readings when the thermocouple location is varied between reactor exterior surface and reactor interior. Thus, the temperatures reported in the Examples are actually the temperature of the content of the reactor. In the Examples, the cooling of the reactor to 0° C., cools the content of the reactor to the same temperature. In large reactors, the temperature thermocouple would be placed within the interior of the reactor to provide the actual interior temperature, such as reaction temperature, decomposition temperature, cooling temperature, as the case may be.

Example 1

Vent-Charge Process (Staged Synthesis)

In a 400 mL shaker tube as the reactor was charged iodine (50.8 grams, 0.2 moles) and the intended HFPO quantity (hexafluoropropylene oxide) (116 grams, 0.70 moles) was charged into the reaction in a 3-stage cycle. Each transfer was through a cool-evacuation process. The maximum pressure within the reactor during each stage is reported in Table 1.

Stage I: First portion of HFPO (38.7 grams, 0.233 moles) was transferred into the reaction tube. The tube was heated at 190° C./4 hrs (step (a)), then at 230° C. for 1 hr. The tube was cooled to 0° C. (step (b)), and the gas phase material was released and removed, i.e. vented (step (c)), (and then passed through a scrubber with 40% KOH/aqueous solution);

Stage II: The reaction tube was further cooled to −78° C. in a dry-ice/acetone bath, then the second portion of HFPO (38.7 grams, 0.233 moles) was transferred into the reaction tube. The tube was heated at 190° C./4 hrs (step (a)), then at 230° C. for 1 hr; the tube was again cooled to 0° C. (step (b)), and the gas phase material was vented (step (c));

Stage III: The reaction tube was further cooled to −78° C. in a dry-ice/acetone bath, then the third portion of HFPO (38.7 grams, 0.233 moles) was transferred into the reaction tube. The tube was heated at 190° C./4 hrs final step (a)), then at 230° C. for 8 hr; the final product mixture, after final steps (b) and (c), was worked up by sodium bisulfite wash as previously described. The total amount of HFPO reacted with the iodine was 3.5 mols of the HFPO/per mol of iodine. The resultant purified reaction product (73.0 grams, 85.1%) was examined by GC. PDA-3 has an area 72.2%, and PDA-1 and PDA-2 has an area 0.05% and 0.02 area % respectively. All the PDAs detected accounted for 97.47 area % of the entire purified reaction product.

Like results are obtained when the heating to 230° C. is carried out only on the direct reaction product resulting from the final step (a).

Example 2

Example 1 was repeated except that added catalyst was present in the shaker tube for each stage of the reaction. The catalyst added to the shaker tube was 5 g Ni ProPack® plus 10 g. Mo wire. The result of this experiment was 73.7 g (86.0% yield) of purified reaction product giving the following GC analysis: PDA-1=0.17 area %, PDA-2=0.00 area %, PDA-3=81.30 area %, PDA-4=1.50 area %, PDA-5=12.50 area %, PDA-6=1.15 area %, and PDA-7=0.97 area %, totaling 97.59 area %. The benefit of the added catalyst is primarily reducing the small amount of PDA-2 from 0.02 area % of Example 1 to non-detectible.

Comparison Example A

Single Stage Synthesis, Single Venting

A batch of diiodoperfluoroalkanes was produced with no added catalyst using the same quantities of iodine and HFPO as for Example 1. In a 400 mL shaker tube as the reactor was charged iodine (50.8 grams, 0.2 moles) and HFPO (116 grams, 0.70 moles) was charged through a cool-evacuation process. The tube was heated at 190° C. for 8 hrs, and at 230° C. for 6 hrs. The maximum pressure measured during the reaction is reported in Table 1. The tube was cooled, then PAF was vented and then quenched with 40% KOH/aqueous solution. The liquid reaction product was collected, then washed with saturated sodium bisulfite aqueous solution to afford 78.6 g (91.7%) of purified reaction product giving the following GC analysis: PDA-1=0.11 area %, PDA-2=0.02 area %, PDA-3=74.8 area %, PDA-4=2.58 area %, PDA-5=17.7 area %, PDA-6=2.01 area %, and PDA-7=2.25 area %, totaling 99.47 area %.

TABLE 1

Maximum Reactor Pressure Measured During Heating in Examples 1 and 2 and the Comparison Example

| | Maximum Pressure (MPa) | | | |
|---|---|---|---|---|
| | Staged Synthesis/Venting | | | Single |
| Example | Stage 1 | Stage 2 | Stage 3 | stage |
| 1 | 3.6 | 3.6 | 3.6 | — |
| 2 | 3.5 | 3.5 | 3.5 | — |
| Comp Ex A | — | — | — | 7.2 |

The data shows that the vent-charge process (staged synthesis) of this Invention greatly reduces the maximum pressure of the process while maintaining good yields and product selectivity. This pressure reduction can be increased by increasing the stages to greater than 3.

What is claimed is:

1. A process of forming the reaction product comprising the homologue mixture of $I(CF_2)_nI$, wherein n is 3 to 7, which contains at least one of the contaminants $ICF_2I$ and $I(CF_2)_2I$, by the steps comprising
   (a) reacting iodine with hexafluoropropylene oxide at a temperature of 150° C. to 210° C. in a reactor, the amount of said hexafluoropropylene oxide being a portion of the total amount of hexafluoropropylene oxide to be reacted with said iodine, thereby forming a reaction product containing gaseous perfluoroacetyl fluoride as a reaction by-product,
   (b) cooling said reaction product to become liquid except for said gaseous perfluoroacetyl fluoride,
   (c) venting said perfluoroacetyl fluoride from said reactor, and
   (d) repeating said steps (a), (b), and (c) until said total amount of said HFPO is reacted with said iodine,
   and obtaining as a result thereof said reaction product comprising said homologue mixture.

2. A process of forming the reaction product comprising the homologue mixture of $I(CF_2)_nI$, wherein n is 3 to 7, which contains at least one of the contaminants $ICF_2I$ and $I(CF_2)_2I$, by the steps comprising
   (a) reacting iodine with hexafluoropropylene oxide at a temperature of 150° C. to 210° C. in a reactor, the amount of said hexafluoropropylene oxide being a portion of the total amount of hexafluoropropylene oxide to be reacted with said iodine, thereby forming a reaction product containing gaseous perfluoroacetyl fluoride as a reaction by-product,
   (b) cooling said reaction product to become liquid except for said gaseous perfluoroacetyl fluoride,
   (c) venting said perfluoroacetyl fluoride from said reactor, and
   (d) repeating said steps (a), (b), and (c) until said total amount of said HFPO is reacted with said iodine,
   and obtaining as a result thereof said reaction product comprising said homologue mixture,
   wherein the portion of said hexafluoropropylene oxide reacted in each of said step (a) is from 10 to 50% of said total amount of said hexafluoropropylene oxide reacted with said iodine.

3. The process of claim 1 wherein the molar proportion of said total amount of said hexafluoropropylene oxide reacted with said iodine is at least 3.0.

4. The process of claim 1 wherein the yield of said reaction product after step (d) is at least 70%.

5. The process of claim 1 wherein said homologue mixture of $I(CF_2)_nI$, wherein n is 3 to 7 resulting in the carrying out of said process comprises at least 90% (GC area) of said reaction product.

6. The process of claim 1 wherein said contaminants $ICF_2I$ and $I(CF_2)_2I$, are present in said reaction product in amounts of no greater than 1% and no greater than 0.1%, respectively.

7. The process of claim 1 further comprising heating said reaction product to at least 220° C. at least after the last step (a) of said repeating said steps (a), (b) and (c).

8. The process of claim 1 wherein said reacting in step (a) is carried out in the presence of catalyst.

9. The process of claim 8 wherein said reacting step is carried out in the absence of added catalyst.

* * * * *